United States Patent [19]
Greenlee

[11] Patent Number: 5,110,972
[45] Date of Patent: May 5, 1992

[54] PROCESS FOR RECYCLING SILICONE SCRAP AND PRODUCTS RELATING THERETO

[75] Inventor: Thomas W. Greenlee, Shaker Heights, Ohio

[73] Assignee: Tremco Incorporated, Cleveland, Ohio

[21] Appl. No.: 732,279

[22] Filed: Jul. 18, 1991

[51] Int. Cl.$^5$ .............................................. C07F 7/08
[52] U.S. Cl. .................................................. 556/460
[58] Field of Search ....................... 556/460, 461, 462

[56] References Cited

U.S. PATENT DOCUMENTS

| | | | |
|---|---|---|---|
| 3,803,195 | 4/1974 | Nitzsche et al. | 556/460 X |
| 4,032,557 | 6/1977 | Spörk et al. | 556/460 X |
| 4,113,760 | 9/1978 | Frey et al. | 556/460 X |
| 4,764,631 | 8/1988 | Halm et al. | 556/460 X |

*Primary Examiner*—Arthur C. Prescott
*Attorney, Agent, or Firm*—Nestor W. Shust; Konrad H. Kaeding

[57] ABSTRACT

The present invention relates generally to the re-utilization of silicone scrap material. More specifically, the process of the present invention is directed to dissolving silicone scrap in an appropriate solvent and chemically converting the scrap into dimethyl silicone cyclic trimer, tetramer, pentamer and/or the like by means of a two step acid/base catalyzed cracking process.

5 Claims, No Drawings

PROCESS FOR RECYCLING SILICONE SCRAP AND PRODUCTS RELATING THERETO

FIELD OF THE INVENTION

The present invention relates generally to the re-utilization of silicone scrap material. More specifically, the process of the present invention is directed to dissolving silicone scrap in an appropriate solvent and chemically converting the scrap into dimethyl silicone cyclic trimer, tetramer, pentamer and/or the like by means of a two step acid/base catalyzed cracking process.

BACKGROUND OF THE INVENTION

Chemical waste and scrap material is of increasing concern to society, and as a result, the chemical industry is increasingly focusing its attention on the recycling and re-using of chemical materials.

Silicones, otherwise known as organosiloxanes, are polymeric materials having alternate silicon and oxygen atoms with various organic radicals attached to the silicon. These compositions can be liquid, semisolid or solid, depending upon the molecular weight and degree of crosslinking. Such polymers may be chain extended and/or crosslinked chemically, with or without catalyst.

Silicones are generally stable over temperature ranges from about −50° to about +250 ° C. and sold in the form of fluids, powers, emulsions, solutions resins, pastes, elastomers and the like. Liquid silicones are used in adhesives, sealants, lubricants, protective coatings, coolants, mold-release agents, dielectric fluids, heat transfer, wetting agents and surfactant, foam stabilizer for polyurethanes, diffusion pumps, antifoaming agent for liquids, textile finishes, water repellents, weatherproofing concrete, brake fluids, cosmetic items, polishes, foam shields for solar energy collectors and rust preventives. Silicone resins are used in coatings, molding compounds, laminates (with glass cloth), filament winding materials, room temperature curing cements, electrical insulation, impregnating electric coils, bonding agents, modifiers for alkyd resins, and vibration damping devices. Elastomer or silicone rubber is used in encapsulation of electronic parts, electrical insulation, gaskets, surgical membranes and implants automobile engine components, flexible windows for face masks, sealants, air locks and the like.

Once used, silicones generally cannot be melted down and reused. Once crosslinked, molded or reacted, any scrap must generally be discarded.

U.K patent 2,015,550 to Heidingfeldova, et al., is directed to a method of reclaiming siloxanes by dissolving the siloxane in an amine. However, amines produce noxious odors and the overall process is rather inefficient.

U.S. Pat. No. 3,989,733 to Okamotoa, et al., is directed to a process for the preparation of cyclic polydiorganosiloxanes by a complex distillation process having a vertical packed catalysts zone with an inlet stream at about the middle of the catalyst zone. The process is run at a pot temperature in excess of about 240° C. and is a fix bed, base catalyzed reaction.

U.S. Pat. No. 3,714,213 to Ryan is directed to a method for making cyclopolysiloxanes by cracking the poly(siloxanes) over acid-treated clay or synthetic aluminum silicate. A drawback to this method is that it must be conducted at extreme temperatures.

In *Chemistry of Materials*, Vol. 1, 445-451, 1989, "Synthesis of Cyclic Siloxanes by the Thermal Depolymerization of Linear Poly(siloxanes)" is directed to a fixed bed, acid catalyzed distillation process run at temperatures of from about 500° C. to about 700° C.

As exemplified by the above references, the thermal depolymerization of linear poly(siloxanes) has generally been achieved by either an acid catalyzed cracking reaction or a base catalyzed cracking reaction, typically in combination with temperatures in excess of 180° C. Cracking reactions less than about 180° C. have been achieved by use of an amine solvent, but such processes have proven to be inefficient and have a tendency to produce noxious odors.

It is therefore and object of the present invention to provide a process for recycling silicone materials which is efficient, which can be accomplished at temperatures less than about 180° C., which does not have a tendency to produce noxious odors and which is sufficiently economical to justify full scale commercialization. Other objects and features of the present invention will become apparent to those of ordinary skill in the art upon a further reading of this specification and accompanying claims.

SUMMARY OF THE INVENTION

In accordance with the present invention, high molecular weight silicone elastomers are cracked to useful, low molecular weight, silicone cyclics. Such cyclics can be used as raw materials for synthesizing linear silicone prepolymers.

The preferred process of the present invention requires three steps. The first step involves dissolving the silicone scrap in a solution of an appropriate acid in an appropriate solvent. The preferred solvent of the present invention is Butyl Carbitol TM (diethylene glycol monobutyl ether) or Koppers' Methylnaphthalene Fraction TM (73–78 wt. % alkylnaphthalenes, 3–8 wt. % naphthalene, 5–8 wt. % biphenyl, 5–10 wt. % acenaphthene, 1–5 wt. % dibenzolfuran).

Alternative solvents are identified in Table 1, and as can be seen by this table, triglyme and Methyl Cellosolve would be possible useful solvents, but are less preferred due to their high cost and hazardous nature, respectively. Water, diethylene glycol and tripropylene glycol were generally ineffective in aiding the dissolution of the scrap, suggesting that all highly hydroxylated materials would be poor media for this step; these solvent do not swell cured silicone, so perhaps, if an additive could be found to cause such swelling, such hydroxylated solvents might be useful.

The preferred solvent for the cracking reaction must not only promote the cracking reaction, but also must be easy to separate from the silicone cyclic end product and the solid byproducts. It may also be necessary to remove dissolved impurities from the solvent. The solvent should have a substantially higher boiling point than the silicone cyclics, so that substantially pure silicone cyclics can be distilled from the solution. The solvent generally should be water insoluble, so that water soluble by-products, impurities and the like can be extracted from the solvent in a water extraction process or the like. Ordinary skill and experimentation after reading the present specification may be necessary in choosing an alternative solvent for any alternative embodiment of the present invention.

The first step of the process of the present invention also requires the addition of an acid catalyst. The most preferred acid catalyst is sulfuric acid. However ordinary skill and experimentation may be necessary in choosing an alternative acid catalyst for any alternative embodiment of the present invention.

In the first step, the silicone scrap is dissolved in the solvent comprising the acid catalyst, and the mixture is heated, preferably to a temperature between about 150° C. and 180° C. The high temperature and acid catalyst then causes the dissolution of the silicone scrap. For the acid cracking reaction, useful ratios appear to be in the range of about 39 weight percent silicone scrap, about 57.5 weight percent solvent and about 2.5 weight percent concentrated sulfuric acid.

The cracking reaction is then driven to completion by a second step of the process of the present invention. In this second step, the temperature of the solution is reduced to about 80° C. to about 115° C. and a base catalyst is added to the solution, most preferably, potassium hydroxide. The base catalyzed reaction at the lower temperature drives the cracking reaction substantially to completion. Ordinary skill and experimentation may be necessary after reading this specification for choosing an alternative base for any alternative embodiment of the present invention.

The potassium hydroxide and additional solvent are added, and the final weight ratio (ignoring reactions) is preferably about 31.5 weight percent silicone scrap, about 63 weight percent solvent, about 2 weight percent concentrated sulfuric acid and about 3.5 weight percent potassium hydroxide.

At the end of the potassium hydroxide catalyzed cracking reaction, the reaction mixture consists primarily of silicone cyclics, solid potassium compounds, filler (i.e., fume silica) from the original silicone scrap and solvent. If the solvent boils substantially higher than the expected cyclic tetramer and pentamer, then these products can be distilled out in fairly pure state. No solvent need be distilled. Solvent and silicone cyclic boiling points appear in Table 2.

Filtration of the distillation residue probably is not much affected by choice of solvent. However, cleaning up the solvent may be easier if it is water insoluble. Dissolved impurities might include potassium salts of sulfated or sulfonated solvent. These could be easily removed by water extraction form a water insoluble solvent, while a water soluble solvent would require a second distillation for separation.

In the third step of the process of the present invention, the silicone cyclics are distilled from the reaction mixture. This step allows for the distillation of substantially pure silicone cyclic vapors which in turn can be liquified by means of a water-cooled condensation chamber or the like.

Although the process is preferably a batch, three step process, a continuous process is conceivable. In a continuous process, it is theorized that a tube flow reactor could be used and operated at atmospheric pressure, wherein the reactor is vented to the atmosphere, and the silicone cyclic vapors are condensed by a condenser prior to reaching the exhaust outlet. At one stage of the tube reactor, the solvent could be heated to about 160° C. and sulfuric acid and scrap material could be added. Downstream, the solution could be cooled to about 100° C. and potassium hydroxide could be added. Further downstream, a water extraction could be conducted to remove the sulfuric acid, potassium hydroxide, salts thereof and any byproducts from the reaction.

Thereafter the solvent could be recycled into the initial stage of the continuous reactor.

Generally, the preferred batch process of the present invention yields about 80-95% by weight based upon the silicone available in the scrap or 45-55% by weight based upon the weight of the scrap used. Preferably, the temperature of the distillation is adjusted so that only cyclics are distilled from the reaction mixture. Generally speaking, the cyclics produced are dimethyl silicone cyclic trimer, tetramer, pentamer or the like.

The resulting cyclics can then be used as raw materials to prepare the silanol and vinyl terminated linear silicone prepolymers used in, for example, silicone sealants.

DETAILED DESCRIPTION OF THE PREFERRED EMBODIMENT

The preferred embodiment of the present invention is directed to two-step catalyzed cracking of silicone scrap. In accordance with the present invention, silicone scrap can be defined as liquids or elastomeric solids comprising high molecular weight (i.e., solid) networks of silicone polymer having a siloxane backbone and pendant lower alkyl, typically methyl, groups. A typical cracking reaction can be defined as follows:

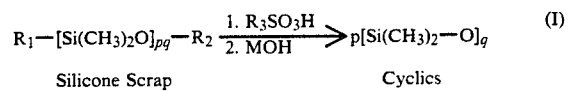

where:
$q \geq 3$, typically 4,
$p$ = is a sufficiently high number to indicate a polymeric material,
$R_1$ and $R_2$ = can be the same or different and are any conventional silicone end groups such as an alkyl group,
$R_3$ = an alkyl, aryl or hydroxide group, and
M = lithium, sodium, potassium, rubidium, cesium, tetraalkylammonium, or tetraalkylphosphonium.

The resulting cyclics can be used as raw materials for linear silicone prepolymers according to any one of a number of reactions, such as:

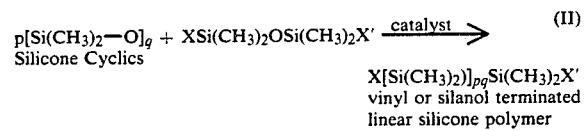

wherein: X and X' can be the same or different and are vinyl or hydroxyl groups.

The product of reaction II, vinyl or silanol terminated linear silicone polymer, is a common starting material for many sealant and mold making materials. A typical curing reaction for such materials is:

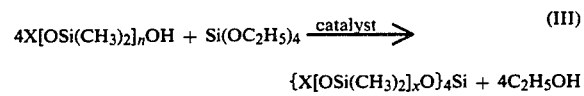

wherein "n" is a number sufficient to indicate a liquid

In the first step of the preferred process of the present invention, the silicone scrap is dissolved in an appropriate solvent. The most preferred solvent comprises sulfuric acid in Butyl Carbitol ™ or Koppers' Methylnaphthalene Fraction ™. Alternative solvents are identified in Table 1, and as can be seen by this Table, triglyme and Methyl Cellosolve ™ (ethylene glycol monomethyl ether) would be possible useful solvents, but are less preferred due to their high cost and hazard potential, respectively. Water, diethylglycol and tripropylene glycol solutions were generally ineffective in dissolving the scrap, suggesting that all highly hydroxylated materials would be poor media for this step. These solvents do not swell cured silicone, so perhaps, if a additive could be found to cause such swelling, such hydroxylated solvents might be useful.

The preferred solvent must not only promote the cracking reaction, but also must be easy to separate from the silicone cyclics and other byproducts subsequent to the base catalyzed cracking reaction. If the solvent boils substantially higher than the expected cyclic tetramer and pentamer, then these products can be distilled out in fairly pure state. No solvent need be distilled. Solvent and cyclic boiling points appear in Table 2. Ordinary skill and experimentation may be necessary after reading this specification in determining an alternative solvent for any alternative embodiment of the present invention.

Once an appropriate solvent is chosen (the most preferred being Butyl Carbitol ™ or Koppers' Methylnaphthalene Fraction ™ ), an acid catalyst is added. The most preferred acid catalyst is sulfuric acid, but alternative acids are conceivably possible and ordinary skill and experimentation may be necessary after reading this specification in determining an alternative acid catalyst for any alternative embodiment of the present invention. Thereafter, the silicone scrap is added, and the mixture is heated to about 150°-180° C. For the acid cracking reaction, useful ratios appear to be in the range of about 39 weight percent silicone scrap, about 57.5 weight percent solvent and about 2.5 weight percent concentrated sulfuric acid.

In the second step of the present invention, the cracking reaction is driven to substantial completion by the reduction of the solution temperature to about 80° C.-115° C. and the addition of an appropriate base catalyst, preferably potassium hydroxide (sodium and calcium hydroxide are less preferred since they tend to give lower cyclic yields than potassium hydroxide). The potassium hydroxide is preferably added as a solid, along with more of the same solvent as chosen for the acid catalyzed cracking reaction. Preferably, the potassium hydroxide and additional solvent are added so as to provide a final weight ratio (ignoring reactions) of about 31.5 weight percent silicone scrap, about 63 weight percent solvent, about 2 weight percent concentrated sulfuric acid and about 3.5 weight percent potassium hydroxide.

In the final step of the process of the present invention, the silicone cyclics are distilled in substantially pure form. The cyclics arise from the initial acid catalyzed, high temperature cracking reaction, followed by the subsequent base catalyzed, lower temperature cracking reaction. In combination, the two step cracking reaction provides a yield of about 80-95% by weight based upon the silicone available in the scrap or 45-55% by weight based upon the weight of the scrap used.

In distilling out the cyclics, the temperature of the distillation should be adjusted so that only cyclics are distilled from the reaction mixture. Generally speaking, the cyclics produced are dimethyl silicone cyclic trimer, tetramer, pentamer or the like.

The resulting cyclics can then be used as raw materials to prepare the silanol and vinyl terminated linear silicone prepolymers used in silicone sealants. Filtration of the distillation residue probably is not much affected by choice of solvent. However, cleaning up the solvent may be easier if it is water insoluble. Dissolved impurities might include potassium salts of sulfated or sulfonated solvent. These could be easily removed by water extraction form a water insoluble solvent, while a water soluble solvent would require a second distillation for separation.

EXAMPLE

D. Cracking Reaction Conditions

Silicone scrap (20.0 g), solvent (30 ml), and concentrated sulfuric acid (50 drops = 1.29 g) were combined in a 250 ml three neck round bottom flask equipped with Teflon paddle stirrer, thermometer, and six inch vacuum jacketed Vigreux condenser equipped for vacuum distillation. The vacuum pump was protected by a Dry Ice-isopropyl alcohol condenser.

Heating and slow stirring were begun at atmospheric pressure under air. Temperature was held at 150°-180° C. for about an hour. Traces of water in the mixture would sometimes make the mixture foam; in these cases, vacuum was cautiously applied to remove the water. Eventually, all silicone scrap would dissolve, giving an opaque gray liquid. No silicone cyclic could be distilled from this mixture; it apparently contained silicone as linear oligomers.

The acid cracking reaction mixture was then let cool with continued stirring to about 50° C. Potassium hydroxide (2.2g) was then added, and heating resumed at a pressure of about 12-18 torr. This vacuum is used only to prevent dense foam in the reaction vessel as the boiling point of silicone cyclic is approached. Without vacuum, the foamy pot material would tend to move up the distillation column.

After the potassium hydroxide dissolves, there is no further visible change in the pot contents. Pot temperature is slowly raised to about 115° C. (No distillate has come over before this temperature.) Schlieren at a distillation temperature of about 85° C. show that some solvent is beginning to come over. By 95° C., solvent comprises most of the distillate.

Distillate and cold trap condensate were weighted an analyzed via gas chromatography. Trap residues amounted to a few grams, about equal parts water and organic layer.

E. Yield of Silicone Cyclics

Actual yield of cyclics was taken as the weight of distillate and trap residue times the weight fraction of silicone cyclic in these phases. Yields of dimethylsilicone cyclics were generally 9-11 g from 20 g of silicone scrap. Both Silastic E (from Dow Corning ™ ) and scrap of unknown origin gave cyclic yields in this range.

Thermogravimetric analysis of these silicone elastomers shows them to be about 45 wt. % filler, or about 55% silicone polymer. Thus in each 20 g scrap sample, there was about 11 g of actual polymer. Recovery of 9-11 g silicone cyclic thus corresponds to 80-100% recovery of the silicone available in the scrap.

TABLE 1

SOLVENT PERFORMANCE[1]

| Solvent | H$_2$SO$_4$ Cracking Reaction | KOH Cracking Reaction |
|---|---|---|
| Triglyme[2] | ++ | ++ |
| 1-Methylnaphthalene | + | + |
| Water | 0 | ? |
| Aliphatic Hydrocarbon | + | ? |
| Diethylene Glycol | 0 | ? |
| Methyl Cellosolve TM[3] | ++ | ++ |
| Tripropylene Glycol | 0 | ? |
| Lauryl Alcohol | + | 0 |
| Aliphatic Oil | + | 0 |
| N,N-Dimethylacetamide | ? | ++ |
| N-Methylpyrrolidinone | ? | 0 |
| N,N',N'-Tetramethylurea | ? | + |
| Dimethyl Sulfoxide | ? | + |
| Sulfolane | ? | 0 |
| 3-Methylsulfolane | ? | 0 |
| Polyoxyethylene | 0 | 0 |
| Diphenyl Ether | ++ | 0 |
| 2-Pyrrolidinone | 0 | 0 |
| Butyl Carbitol TM[4] | ++ | ++ |
| Tripropylene Glycol Monomethyl Ether | 0 | + |

[1] About 1 gram silicone scrap held at 180° F. for three days in the presence of 0.3 g conc H2SO4 in 10 ml solvent, and in the presence of 0.5 g KOH in 10 ml solvent. "0" indicates no turbidity in the solution. "+" indicates a small amount of turbidity, and "++" indicates significant turbidity. "?" indicates that the test was not run.
[2] triethylene glycol dimethyl ether
[3] diethylene glycol monomethyl ether
[4] diethylene glycol mono-n-butyl ether

TABLE 2

BOILING POINTS, °C.

| Material | Atmospheric Pressure | Reduced Pressure |
|---|---|---|
| Dimethylsilicone, Cyclic Tetramer | 175-6 | ~85/18 torr |
| Dimethylsilicone Cyclic Pentamer | 205 | 101/20 torr |
| Triglyme[1] | 216 | 111-112/18 torr |
| 1-Methylnaphthalene | ~240 | 171/17 torr |
| Diethylene Glycol | 244 | |
| Methyl Cellosolve TM[2] | 124 | |
| Lauryl Alcohol | 260-2 | 138/13 torr |
| Dimethylacetamide | 163-5 | |
| N-Methylpurrolidinone | 202 | |
| N,N,N'N'-Tetramethylurea | 176.5 | 63-64/12 torr |
| Dimethyl Sulfoxide | 189 | |
| Sulfolane | 285 | |
| 3-Methylsulfolane | 276 | |
| Diphenyl Ether | 259 | ~130/15 torr |
| 2-Pyrrolidinone | 245 | |
| Butyl Carbitol TM[3] | 231 | |
| Tripropylene Glycol | | 121-2/14 torr |
| Monomethyl Ether Koppers Methylnaphthalene Fraction[4] | 230-75 | |

[1] triethylene glycol dimethyl ether
[2] diethylene glycol monomethyl ether
[3] diethylene gylcol mono-n-butyl ether
[4] 73-78 wt. % alkylnaphthalenes, 3-8 wt. % naphthalene, 5-8 wt. % biphenol, 5-10 wt. % acenaphthene, and 1-5 wt. % dibenzofuran.

TABLE 3

PROPERTIES OF SILANE ELASTOMERS

| | Silicone Scrap A[1] | Silastic E TM[2] |
|---|---|---|
| Appearance | Turbid brownish gray | Opaque white |
| Chief filler | Fume silica | Fume silica[3] |
| Filler loading via TGA[4] | 43.8 wt. % | 45.7 wt. % |
| Wt. loss, THF[5] extract | 7.2 wt. % | <1 wt. % |
| Wt. loss, heptane extract | 1.4 wt. % | <1 wt. % |
| Extracted material, via IR | dimethylsiloxane polymer | dimethylsiloxane polymer |

[1] identity unknown
[2] product of Dow Corning Corporation
[3] titanium dioxide also present
[4] thermogravimetric analysis
[5] tetrahydrofuran

What is claimed is:

1. A process of cracking high molecular weight silicone polymer, said process comprising the steps of:
    dissolving the silicone polymer in an organic solution comprising an acid and heating the resulting mixture until the silicone polymer is substantially dissolved;
    adding a base; and
    distilling out silicone cyclics from the solution.

2. The process of claim 1 wherein the acid is sulfuric acid and the mixture is heated to a temperature in the range of about 150° C. to about 180° C. prior to the adding of the base.

3. The process of claim 2 wherein the base is potassium hydroxide and after the temperature of the solution is raised to about 150° C. to about 180° C., it is then decreased to about 80° C. to about 115° C.

4. The process of claim 3 wherein the final weight ratio of the solution (ignoring reactions) is about 31.5 weight percent silicone polymer, about 63 weight percent solvent, about 2 weight percent concentrated sulfuric acid and about 3.5 weight percent potassium hydroxide.

5. The product of the process of claim 1.

* * * * *